(12) United States Patent
Engel

(10) Patent No.: US 7,887,817 B2
(45) Date of Patent: Feb. 15, 2011

(54) PROCESS FOR PREVENTING PROTOZOAL DISEASES

(75) Inventor: Jürgen Engel, Alzenau (DE)

(73) Assignee: AEterna Zentaris GmbH, Fraankfurt am Main (DE)

( * ) Notice: Subject to any disclaimer, the term of this patent is extended or adjusted under 35 U.S.C. 154(b) by 714 days.

(21) Appl. No.: 10/347,178

(22) Filed: Jan. 8, 2003

(65) Prior Publication Data

US 2003/0216355 A1    Nov. 20, 2003

Related U.S. Application Data

(60) Provisional application No. 60/351,785, filed on Jan. 25, 2002.

(51) Int. Cl.
- *A61K 39/00* (2006.01)
- *A61K 39/002* (2006.01)
- *A61K 39/38* (2006.01)
- *A01N 25/28* (2006.01)
- *A01N 25/34* (2006.01)

(52) U.S. Cl. .............. 424/265.1; 424/1.65; 424/184.1; 424/191.1; 424/269.1; 424/404; 424/418; 424/435

(58) Field of Classification Search ............. 424/269.1, 424/270.1, 271.1, 272.1, 273.1; 435/41, 435/243, 258.1, 258.3
See application file for complete search history.

(56) References Cited

U.S. PATENT DOCUMENTS 5,980,915 A * 11/1999 Eibl et al. ............ 424/401
5,985,935 A    11/1999 Kharazmi et al.
6,544,551 B1    4/2003 Engel

FOREIGN PATENT DOCUMENTS

| DE | 41 32 344 A 1 | | 4/1993 |
|---|---|---|---|
| DE | 41 32 345 A 1 | | 4/1993 |
| DE | 100 20 812 A 1 | | 10/2001 |
| WO | WO 99/37289 | * | 7/1999 |
| WO | WO 02/36588 A2 | | 5/2002 |

OTHER PUBLICATIONS

Fichoux et al. 1998. Antimicrobial Agents and Chemo. vol. 42(3): 654-658.*
Jha et al. 1999. New England J. of Medicine. vol. 341(24): 1795-1800.*
Sundar et al. 1999. Annals of Tropical Medicine and Parasitology. vol. 93(6): 589-597.*
See The Division of Parasitic Diseases—Leishmania Infection Fact Sheet. WWW.cdc.gov/Ncidod/dpd/parasites/leishmania/factsht_leishmania.htm.*
Davies et al. 2003. BMJ. vol. 326:377-382.*
Reed. 2001. J. Exp. Med. vol. 194(3): F7-F9).*
Reed. 2001. J. Exp. Med. vol. 194(3): F7-F9.
Jha et al. 1999. The New England Journal of Medicine. vol. 341(24):1795-1800.
Prof. Dr. Eibl: Tödliche Tropenkrankheit jetzt heilbar, Max-Planck-Institut für Biophysikalische Chemie, 'Online!, Jan. 28, 2000, XP002239911, pp. 1-5.
PCT Search Report.
German Patent and Trademark Office Search Report.

* cited by examiner

*Primary Examiner*—Larry R Helms
*Assistant Examiner*—J. Hines
(74) *Attorney, Agent, or Firm*—Goodwin Procter LLP

(57) ABSTRACT

A process for preventing a protozoal disease by the administration of an alkyl phosphocholine to a human being.

12 Claims, No Drawings

PROCESS FOR PREVENTING PROTOZOAL DISEASES

This is a nonprovisional application based on provisional application Ser. No. 60/351,785, filed on Jan. 25, 2002.

FIELD OF THE INVENTION

The present invention relates to alkyl phosphocholines, especially to pharmaceutical compositions containing hexadecyl phosphocholine (miltefosin) or octadecyl 1,1-dimethyl-piperidino-4-yl phosphate (perifosin, D-21266) for oral administration for the preventive treatment of protozoal diseases, especially of leishmaniasis. The invention furthermore relates to a dosage plan for the oral administration of this pharmaceutical composition for the preventive treatment of protozoal diseases, especially leishmaniasis, and a combination, which comprises this pharmaceutical composition, an anti-emetic and/or an antidiarrheal agent.

BACKGROUND

Leishmaniasis is the collective name for various tropical diseases, which are caused by flagellates of the leishmania species and are transmitted by various blood-sucking insects. The manifestations of leishmaniasis can be visceral (kala-azar), mucocutaneous (American leishmaniasis) or cutaneous (Aleppo boil or diffuse skin leishmaniasis). The incubation time ranges from weeks to months. A very high mortality rate is observed in untreated cases, especially in the case of kala-azar and the American leishmaniasis Five-valent antimony compounds are the agent of choice in the standard therapy for the treatment of leishmaniasis diseases, such as sodium stilbogluconate, and aromatic diamidines which must be administered by parenteral injection. This not only leads to serious side effects because of the high toxicity of these materials, but also harbors the risk of infection.

The suitability of alkyl phosphocholines, especially hexadecyl phosphocholine (miltefosin) for the oral and topical treatment of leishmaniasis, was described for the first time by Eibl et al. in German patent application No. 4,132,344 and in European application No. 534,445, both of which were filed in 1991.

Numerous other authors describe the treatment of leishmaniasis with alkyl phosphocholines as a new class of medicinal drugs with remarkable antiprotozoal effectiveness. For example, T. Jha et al., Miltefosine, an oral agent, for the treatment of Indian visceral leishmaniasis, N. Engl. J. Med. (1999), 341(24), 1795-1800 reported a study with 120 patients, to whom 50 to 150 mg of miltefosin per day was administered over a period of several weeks. In a pilot trial. Sundar et al., Oral treatment of visceral leishmaniasis with miltefosine, Ann. Trop. Med. Parasitol. (1999), 93(6), 589-597 observed the oral use of 100 to 200 mg of miltefosin per day in the case of visceral leishmaniasis.

Miltefosin is difficult to handle, because it is very hygroscopic, although it can be obtained in dry form as crystalline platelets with a defined melting point over 200° C. The absorption of water molecules can lead to an increase in weight of up to 30%, to a lowering of the melting point and to an agglomeration and lumping of crystals. Water-containing miltefosin cannot be adequately further processed into pharmaceutical preparations such as tablets, capsules or sachets. In particular, the flowability of water containing miltefosin is inadequate. However, a satisfactory flowability is one of the indispensable prerequisites for the production of pharmaceutical compositions on an industrial scale.

In addition, anhydrous miltefosin has an appreciable tendency to develop electrostatic charges, especially when it is stirred in the dry state. The flowability of electrostatically charged miltefosin is also inadequate for further processing into solid pharmaceutical compositions. Moreover, electrostatic charging is always associated with appreciable safety concerns because of the risk of explosions as well as damage to sensitive electronic parts.

To get around the above-mentioned problem during the production of pharmaceutical compositions containing solid miltefosin, Eibl et al. proposed that miltefosin be applied to the surface of silica particles in that a suspension of 1 part by weight of silica in a solution with 1 by weight of miltefosin is evaporated to dryness. The flowability of the solid dispersion, obtained in accordance with the proposal of Eibl et al., is in fact adequate for filling capsules at least on a laboratory scale. However, the method described by Eibl et al. is based on the use of a highly volatile solvent which, at the same time, because of the risk of electrostatic charging, is not flammable. For all practical applications, the only solvents, which are known in the art and fulfill these requirements, are methylene chloride and chloroform. However, halogenated hydrocarbons, especially chloroform, are classified as toxic and carcinogenic compounds. Furthermore, halogenated hydrocarbons accumulate in fatty tissue and are broken down only slowly.

It was described in patent publication No. WO 99/37289 that the above-mentioned problems can be solved by physically mixing an alkyl phosphocholine, especially hexadecyl phosphocholine with at least one flow promoter and/or lubricant, selected from the group of finely divided silica, talc, magnesium stearate and mixtures thereof, and at least one filler, from the group of lactose, microcyrstalline cellulose and mixtures thereof.

In accordance with publication WO 99/37289, it is possible, simply by mixing alkyl phosphocholines, especially miltefosin, a flow promoter and/or a lubricant and at least one filler, to obtain a solid pharmaceutical mixture with a flowabililty, which is adequate for further processing, especially into tablets, capsules or sachets.

In accordance with WO 99/37289 the pharmaceutical composition can be filled into capsules, preferably hard gelatin capsules, or pressed into tablets or effervescing tablets or, as a beverage or effervescent mixture, filled into sachets.

The miltefosin content per dose unit ranges from 10 to 800 mg, especially from 10 to 500 mg and particularly from 50 to 250 mg. The most preferred content ranges from 50 to 150 mg.

The production of miltefosin is described in detail in the examples for hexadecyl phosphocholine in the German patent application No. 4,132,344. Further methods for producing and purifying miltefosin are described in the German patent applications Nos. 2,752,125, 3,641,379, 3,641,491, 4,013, 632, and 3,641,377.

DESCRIPTION OF THE INVENTION

It was surprisingly and unexpectedly found according to one aspect of the present invention that alkyl phosphocholines, especially hexadecyl phosphocholine (miltefosin) and octadecyl 1,1-dimethyl-piperidinio-4-yl phosphate (perifosin, D-21266) are suitable for the preventive treatment of protozoal diseases, especially of leishmaniasis. Pharmaceutical administration of alkyl phosphocholines, especially of hexadecyl phosphocholine or of octadecyl 1,1-dimethyl-piperidinio-4-yl phosphate for the prevention of protozoal diseases, especially of leishmaniasis, is neither described nor made obvious in the publications of the state of the art.

In accordance with one aspect of the present invention, a dosage plan is provided for the preventive treatment of leishmaniasis in man by the oral administration of the pharmaceutical composition. In the case of a suitable embodiment of the present invention, the following dosage plan is suitable for the preventive treatment of leishmaniasis in man by oral administration. Total dosage: 10 to 250 mg of miltefosin active ingredient, suitably 20 to 150 mg and especially 30 to 100 mg. Daily single or multiple dose: a total daily dose of 10 to 50 mg of active ingredient is administered suitably as a single daily dose. A dose of 50 to 250 mg of active ingredient and suitably of 50 to 150 mg of active ingredient is administered orally daily as a daily multiple dose, suitably as two doses per day (total daily dose of 100 mg of active ingredient) or as three doses per day (total daily dose of 150 mg). From the point of view of compliance by the patients, a daily dose, divided into four to five doses, is generally regarded as the upper limit. For preventive purposes, however, it is also possible to administer the agent differently than divided into one to five doses per day.

In the case of a suitable embodiment, daily multiple doses of the same magnitude are administered (for example, 100 mg of active ingredient per day=2×50 mg of active ingredient per day or 150 mg of active ingredient per day=3×50 mg of active ingredient per day).

Prophylaxis with an initial dose, followed by maintenance doses is also possible, 100 mg of active ingredient or more, for example, being administered as initial dose, followed by, for example, 30 mg of active ingredient as maintenance doses.

Duration of the prophylactic use: 2 weeks to 6 months, preferably for the duration of the risk of infection.

In accordance with a further aspect of the invention, a dosage plan for the preventive treatment of leishmaniasis in mammals other than man is made available by the oral administration of the inventive pharmaceutical composition.

All mammals can be treated. A preventive treatment of all types of leishmaniasis, especially of Leishmaniasis major and *Leishmaniasis infantum*, is possible with the dosage plan. According to the dosage plan, the total daily dose for the prophylactic treatment in the case of an oral administration ranges from 0.5 to 15 mg of active ingredient (miltefosin or perifosin) per kg of body weight of the animal (mg of active ingredient/kg). In the case of a suitable embodiment, the prophylaxis is commenced with an initial total individual dose (saturation dose) ranging from 3 to 15 and preferably from 5 to 10 mg of active ingredient/kg and then continued with a total daily dose (maintenance dose) training from 1 to 10 and suitably from 3 to 5 mg of active ingredient/kg. The preventive administration ranges from 2 weeks to 6 months and, suitably, for the duration of the risk of infection.

In accordance with a further aspect of the present invention, a combination of the pharmaceutical composition with an anti-emetic and/or an antidiarrheal agent is made available for oral administration for the preventive treatment of leishmaniasis.

In a suitable embodiment of the invention, the pharmaceutical composition is administered in combination with an anti-emetic and/or an antidiarrheal agent. The latter can be administered simultaneously or consecutively. The anti-emetic and the antidiarrheal agent can be administered independently of one another. The anti-emetic and/or the antidiarrheal agent can be contained either in the pharmaceutical composition described or in a pharmaceutical formulation, which is independent thereof.

Suitable anti-emetics are, for example, 5-HT3 receptor antagonists, substituted benzamides, corticosteriods, antihistamines, neuroleptic agents of the phenothiazine type, neuroleptic agents of the butyrophenone type, benzodiazepins and cannabinoids. Suitable anti-emetics include metoclopramide, domperidon and alizaprid.

Suitable antidiarrheal include opiods, such as loperamid.

The solid, oral pharmaceutical compositions are suitably useful for the preventive treatment of leishmaniasis. Other diseases, caused by protozoa, include for example, malaria, trypanosomiasis, toxoplasmosis, babesiosis, amebic dysentery and lambliasis.

EXAMPLES

The invention is explained in greater detail by means of the following examples.

Examples of Solid, Oral Pharmaceutical Formulations, which can be Used

Example 1

Hard Gelatin Capsule (Content: 10 mg of Miltefosin)

Hexadecyl phosphocholine (100 g), 808.5 g of lactose, 448.50 g of microcrystalline cellulose, 26 g of talc and 13 g of finely divided silica are passed through a sieve with a mesh width of 0.8 mm and then homogenized for 30 minutes in a suitable mixer. Magnesium stearate (4 g, 0.8 mm sieve) is then added and the components are mixed for a further 5 minutes. The mixture, so obtained, is filled in 140 mg portions by known procedures into hard gelatin capsules weighing 50 mg, a suitable encapsulating machine being used. Each of the capsules so obtained (total weight: 190 mg) contains 10 mg of hexadecyl phosphate. The ratio of hexadecyl phosphocholines to flow promoter/surfactant to fillers in the mixture is 1:0.4:12.4 (parts by weight).

Example 2

Hard Gelatin Capsule (Content: 100 mg of Miltefosin)

Hexadecyl phosphocholine (1,000 g), 584 g of lactose, 345 g of microcrystalline cellulose, 50 g of talc, 15 g of finely divided silica and 6 g of magnesium stearate are mixed by the method described in Example 1.

The mixture, so obtained, is filled in 200 mg portions by known methods into hard gelatin capsules weighing 76 mg, a suitable encapsulation machine being used for this purpose. Each of the capsules, so obtained (total weight 276 mg), contains 100 mg of hexadecyl phosphocholine. The ratio of hexadecyl phosphocholine to flow promoter to filler in the mixture is 1:0.07:0.9 (parts by weight)

Example 3

Hard Gelatin Capsule (Content: 250 mg of Miltefosin)

Hexadecyl phosphocholine (250 g), 80 g of lactose, 50 g of microcrystalline cellulose, 5 g of talc, 5 g of finely divided silica and 15 g of magnesium stearate are mixed by the method described in Example 1. The mixture, so obtained, is filled in 405 mg portions by known methods into hard gelatin capsules weighing 97 mg, a suitable encapsulating machine being used for this purpose.

Each of the capsules, so obtained has a total weight of 502 mg and contains 250 mg of hexadecyl phosphocholine. The ratio of hexadecyl phosphocholine to flow promoter to filler in the mixture is 1:0.1:0.52 (parts by weight).

Example 4

Hard Gelatin Capsule (Content: 250 mg of Miltefosin)

Hexadecyl phosphocholine (50 g), 24.25 g of microcrystalline cellulose and 22.00 g of anhydrous dicalcium phosphate are screened and mixed. Magnesium stearate (3.75 g) is screened and added to the mixture. The mixture is then mixed once again. The mixture, so obtained, is then pressed into tablets weighing 500 mg each. In each case, the tablets contain 250 mg of hexadecyl phosphocholine. The ratio of hexadecyl phosphocholine to flow promoter/surfactant to fillers in the tablet is 1:0.007:0.925 (parts by weight).

Example 5

Tablets Containing 30 mg of Hexadecyl Phosphocholine

Hexadecyl phosphocholine (23 g), 23 g of microcrystalline cellulose and 52 g spray-dried lactose are screened and mixed. Colloidal silica (1 g) and 1 g of magnesium stearate are added. The mixture is then mixed once again.

The mixture, so obtained, is then pressed into tablets weighing 130.5 mg each. In each case, the tablets contain 30 mg of hexadecyl phosphocholine. The ratio of hexadecyl phosphocholine to flow promoter/surfactant to fillers is 1:0.087:0.31 (parts by weight).

Example 6

Effervescent Tablets and Effervescing Mixture Containing 250 mg of Hexadecyl Phosphocholine Granular sodium hydrogen carbonate (1,700 g) is heated for 60 minutes in an oven at 100° C. After being cooled to room temperature, the converted hydrogen carbonate is mixed with 160 g of granular monobasic calcium phosphate, 1,030 of anhydrous granular citric acid, 100 g of talc and 50 g of magnesium stearate. The mixture, so obtained, is mixed with 300 g of hexadecyl phosphocholine for 10 minutes.

The effervescent mixture, so obtained, is pressed into tablets weighing 278 mg each. In each case, the effervescent tablets contain 250 mg of hexadecyl phosphocholine. The ratio of hexadecyl phosphocholine to flow promoter/surfactant to fillers is 1:0.50:0.53 (parts by weight)

Alternatively, 278 mg of the effervescing mixture can be filled into a sachet, an effervescing mixture being obtained.

Example 7

Effervescent Tablets and Effervescing Mixture Containing 50 mg of Hexadecyl Phosphocholine Granular sodium hydrogen carbonate (1,600 g) is heated for 60 minutes in an oven at 100° C. After being cooled to room temperature, the converted hydrogen carbonate is mixed with 150 g of granular monobasic calcium phosphate, 900 g of granular anhydrous citric acid, 80 g of talc and 30 g of magnesium stearate. The mixture, so obtained, is mixed with 200 g of hexadecyl phosphocholine for 10 minutes.

The mixture, so obtained, is pressed into tablets weighing 740 mg each. In each case, the effervescent tablets contain 50 mg of hexadecyl phosphocholine. The ratio of hexadecyl phosphocholine to flow promoter/surfactant to fillers is 1:0.55:0.75 (parts by weight)

Alternatively, 740 mg of the effervescing mixture can be filled into a sachet, an effervescing mixture being obtained.

Example 8

Beverage Mixture (Sachets, Containing 50 mg of Hexadecyl Phosphocholine

Hexadecyl phosphocholine (5 g), 308 g of lactose, 280 g of microcrystalline cellulose, 5 g of saccharin and 2 g of colloidal silica are mixed. The mixture is filled into sachets, which weigh 6 g each and contain 50 mg of hexadecyl phosphocholine. The ratio of hexadecyl phosphocholine to flow promoter/surfactant to fillers is 1:0.4:117.5 (parts by weight).

Example 9

Beverage Mixture (Sachets, Containing 200 mg of Hexadecyl Phosphocholine

Hexadecyl phosphocholine (20 g), 306 g of lactose, 403 g of microcrystalline cellulose, 5 g of saccharin and 6 g of colloidal silica are mixed. The mixture is filled into sachets, which weigh 7.4 g each and contain 250 mg of hexadecyl phosphocholine. The ratio of hexadecyl phosphocholine to flow promoter/surfactant to fillers is 1:0.3:35.5 (parts by weight).

Instead of miltefosin, the examples can contain perifosin.

I claim:

1. A process for preventing visceral leishmaniasis, which comprises administering to a human in whom prevention of the visceral leishmaniasis is desired a pharmaceutical composition comprising an alkyl phosphocholine selected from the group consisting of hexadecyl phosphocholine (miltefosin), and octadecyl 1,1-dimethyl-piperidino-4-yl phosphate (perifosin), wherein said administration of said pharmaceutical composition is for prophylactic use before the infection of leishmaniasis.

2. The process of claim 1, wherein said alkyl phosphocholine is administered orally at a daily dose, of from about 10 to about 250 mg for a period of 2 weeks to 6 months.

3. The process of claim 1, wherein a total daily dose of about 20 to about 150 mg of miltefosin or perifosin is administered.

4. The process of claim 1, wherein a total daily dose of about 30 to about 100 mg of miltefosin or perifosin is administered.

5. The process of claim 1, wherein the alkyl phosphocholine is miltefosin or perifosin which is administered orally once, twice or three times daily in total daily dose of about 50 mg, about 100 mg, or about 150 mg.

6. The process of claim 1, wherein multiple daily doses are administered in two or three equal portions.

7. The process of claim 1, wherein the administration comprises administration of an initial dose of said alkyl phosphocholine followed by administration of a maintenance dose, wherein the initial dose advantageously contains at least about 100 mg of the alkyl phosphocholine, and the maintenance dose contains at least about 30 mg thereof.

8. The process of claim 1, wherein a daily dose of from about 0.5 to about 15 mg of miltefosin per kilogram of body weight is administered.

9. The process of claim 1, wherein an initial, total, single saturation dose of said alkyl phosphocholine is administered at a concentration of from about 3 mg to about 15 mg per kg of body weight, and a subsequent total daily maintenance dose is from about 1 to about 10 mg of per kg body weight.

10. The process of claim 9, wherein the saturation dose is from about 5 to about 10 mg per kg body weight.

11. The process of claim 9, wherein the subsequent total daily maintenance dose is from about 3 to about 5 mg per kg body weight.

12. The process of claim 1, wherein said alkyl phosphocholine is administered orally over a period of from about 2 weeks to about 6 months.

\* \* \* \* \*